ര
United States Patent [19]

Schraut et al.

[11] Patent Number: 6,051,736
[45] Date of Patent: Apr. 18, 2000

[54] PREPARATION OF (METH)ACRYLIC ACID

[75] Inventors: Armin Schraut, Bensheim; Michael-Dieter Ulbrich, Freinsheim; Freidrich-Georg Martin, Heidelberg; Bernd Eck, Viernheim; Jörg Heilek, Bammental, all of Germany

[73] Assignee: BASF Aktiengesellschaft, Ludwigshafen, Germany

[21] Appl. No.: 09/035,874

[22] Filed: Mar. 6, 1998

[30] Foreign Application Priority Data

Mar. 7, 1997 [DE] Germany ............ 197 09 471

[51] Int. Cl.[7] ............ C07C 51/42; C07C 51/16; C07C 51/21
[52] U.S. Cl. ............ 562/600; 562/532; 562/538; 568/470; 568/492
[58] Field of Search ............ 562/600, 532, 562/538; 568/470, 492

[56] References Cited

U.S. PATENT DOCUMENTS

| | | | |
|---|---|---|---|
| 3,798,264 | 3/1974 | Kubota et al. | 260/526 |
| 3,957,880 | 5/1976 | Sato et al. | 260/604 |
| 3,962,074 | 6/1976 | Schropp | 210/21 |
| 4,234,519 | 11/1980 | Yeoman et al. | 568/492 |
| 4,533,750 | 8/1985 | Matsumura et al. | 562/600 |
| 4,618,709 | 10/1986 | Sada et al. | 562/532 |
| 5,248,819 | 9/1993 | Matsumoto et al. | 562/532 |
| 5,831,124 | 11/1998 | Machhammer et al. | 562/600 |

FOREIGN PATENT DOCUMENTS

| | | | |
|---|---|---|---|
| 14 93 325 | 1/1969 | Germany . | |
| 21 64 767 | 7/1972 | Germany . | |
| 23 23 328 | 11/1974 | Germany . | |
| 1081095 | 8/1967 | United Kingdom . | |
| 2 045 759 | 11/1980 | United Kingdom | C07C 57/07 |

*Primary Examiner*—Ralph Gitomer
*Assistant Examiner*—Marjorie A. Moran
*Attorney, Agent, or Firm*—Oblon, Spivak, McClelland, Maier & Neustadt, P.C.

[57] ABSTRACT

The invention is directed toward preparation of (meth)acrylic acid, comprising condensation of a gas comprising (meth)acrylic acid, absorption with water, and extraction with an aqueous solution forming a miscibility gap.

27 Claims, 3 Drawing Sheets

PREPARATION OF (METH)ACRYLIC ACID

BACKGROUND OF THE INVENTION

Field of the Invention

The present invention relates to a novel process for the preparation of (meth)acrylic acid which comprises a stage in which an aqueous solution which contains (meth)acrylic acid is extracted by being brought into contact with a solution which contains at least one starting material for the preparation of (meth)acrylic acid and forms a miscibility gap with the aqueous solution.

The term (meth)acrylic acid used in this Application refers to both acrylic acid and methacrylic acid.

Owing to its very reactive monoethylenically unsaturated bond and the acid function, methacrylic acid is a useful monomer for the preparation of polymers, for example for aqueous polymer dispersions suitable as adhesives.

Methacrylic acid is obtainable, inter alia, by gas-phase oxidation of 1-butene, isobutene, isobutyraldehyde, isobutyric acid, isobutene, MTBE and/or methacrolein with oxygen or oxygen-containing gases in the presence of catalysts, for example multimetal oxides which contain the elements molybdenum and vanadium in oxidic form. The oxidation is carried out at elevated temperatures and, owing to the considerable heat of reaction, preferably with dilution of the reactants with inert gases, such as $N_2$, $CO_2$ and/or hydrocarbons and/or steam. However, these processes do not give pure methacrylic acid but a reaction mixture which contains, in addition to methacrylic acid, the starting materials, for example unconverted methacrolein, steam, inert diluent gas (e.g. nitrogen) and byproducts (eg. oxides of carbon), lower aldehydes, eg. formaldehyde, high boilers, eg. citraconic acid, and in particular acetic acid, from which the methacrylic acid must subsequently be isolated (cf. for example EP-A 253 409 and DE-A 19 62 431). However, possible starting compounds are also those from which the actual $C_4$ starting compound eg. methacrolein, is first formed as an intermediate during the gas-phase oxidation. An example is the methyl ether of tert-butanol (MTBE).

For the preparation of methacrolein, it is also possible to subject formaldehyde and propionaldehyde to a condensation reaction and to obtain methacrolein by distillation in higher purity than in the processes discussed above. Such a process is described in EP-B 58 927. The methacrolein thus obtained can then be converted into methacrylic acid in a conventional manner by catalytic gas-phase oxidation. Such a reaction is described, inter alia, in EP-B 297 445.

Acrylic acid can be obtained starting from the corresponding $C_3$ compounds, in particular propylene and/or acrolein.

If, in a process for the preparation of (meth)acrylic acid, it is intended to isolate the latter from the resulting reaction gas mixture by extraction, the reaction gas mixture is first subjected to a condensation stage and then extracted. Thus, EP-B 345 083 describes such a process which comprises a methacrylic acid extraction stage in which methacrylic acid is extracted with a saturated hydrocarbon of 6 to 9 carbon atoms.

According to EP-A 710 643, in a process for the purification of methacrylic acid, an aqueous methacrylic acid solution obtained by cooling and condensing the reaction gas is extracted from the aqueous solution by adding an organic solvent, preferably an aliphatic hydrocarbon of 5 to 9 carbon atoms, an aromatic hydrocarbon, an ester or a mixture thereof.

Japanese Patent JP 57 095 938 describes the extraction of acrylic acid from a dilute aqueous solution by extraction by means of an oxygen-containing solvent and a tertiary amine. Examples are trioctylamine and 2,6-dimethyl-4-heptanol.

However, all these processes are disadvantageous in that in each case the extraction of (meth)acrylic acid requires the use of a foreign substance which, on the one hand, is not obtainable without additional costs and moreover, in such a process, necessitates additional steps for separating off this foreign substance again, entailing additional costs and additional energy consumption.

None of the prior art processes describes the possibility of extracting (meth)acrylic acid by means of a solution which contains an alkane, alkanol, alkene or alkenal of 3 or 4 carbon atoms or a mixture of two or more thereof, ie. a starting material for the preparation of (meth)acrylic acid. To date, only foreign substances, as stated above, have been used as extracting agents.

It is an object of the present invention to provide a process for the preparation of (meth)acrylic acid, by means of which the above disadvantages of the processes described to date for the preparation of (meth)acrylic acid can be wholly or partly avoided. A particular feature of the present invention is the extraction of (meth)acrylic acid without the use of foreign substances. Furthermore, this process should be capable of managing with a smaller amount of water and energy compared with the prior art processes.

We have found that these two objects too are achieved by the novel process, which, if desired, can be carried out entirely without distillation stages, which are known to be very energy-intensive.

BRIEF DESCRIPTION OF THE DRAWINGS

For better illustration of the present invention, three Figures are attached to this Application.

SUMMARY OF THE INVENTION

The present invention therefore relates to a process for the preparation of (meth)acrylic acid, which comprises the following stages:

A: Preparation of a reaction gas which contains (meth) acrylic acid, an alkane, alkanol, alkene or alkenal of 3 or 4 carbon atoms or a mixture of two or more thereof, water and oxygen, by gas-phase oxidation of an alkane, alkanol, alkene or alkenal of 3 or 4 carbon atoms or a mixture of two or more thereof under heterogeneous catalysis;

B: Condensation of reaction gas obtained in stage A, a first aqueous solution, which contains the main amount of (meth)acrylic acid and a residual amount of alkane, alkanol, alkene or alkenal of 3 or 4 carbon atoms or the mixture of two or more thereof from the reaction gas, and a first gas phase, which contains the main amount of alkane, alkanol, alkene or alkenal of 3 or 4 carbon atoms or the mixture of two or more thereof and a residual amount of (meth)acrylic acid from the reaction gas, being obtained;

C: Absorption of the (meth)acrylic acid obtained in the first gas phase by bringing the first gas phase into contact with fresh water, a second aqueous solution, which contains (meth)acrylic acid, and a second gas phase, which contains the alkane, alkanol, alkene or alkenal of 3 or 4 carbon atoms or the mixture of two or more thereof, being obtained;

D: Extraction of the second aqueous solution which contains (meth)acrylic acid by bringing said solution into contact with a solution which contains an alkane, alkanol, alkene or alkenal of 3 or 4 carbon atoms or a mixture of two or more thereof and forms a miscibility gap with the second aqueous solution, an organic phase, which contains (meth)acrylic acid and the main part of alkane, alkanol, alkene or alkenal of 3 or 4 carbon atoms or of the mixture of two or more thereof, and a third aqueous solution, which contains a smaller part of alkane, alkanol, alkene or alkenal of 3 or 4 carbon atoms or of the mixture of two or more thereof, being obtained.

DETAILED DESCRIPTION OF THE INVENTION

As is evident from the above, the novel process consists of stages A to D, in particular the extraction of (meth)acrylic acid by means of an alkane, alkanol, alkene or alkenal of 3 or 4 carbon atoms or of a mixture of two or more thereof as an extracting agent (stage D) being regarded as essential to the invention. The remaining stages E and G and KR+FFT described below and the modifications or intermediate stages described herein can be combined with the processes comprising the stages A to D in a manner evident to a person skilled in the art—depending on the type of use and intended use—and in any desired technically useful manner. The following description and the subclaims relate to preferred embodiments of these possible combinations.

The preparation of a reaction gas which contains (meth) acrylic acid, (meth)acrolein, water and oxygen, according to stage A, is known per se and is described, inter alia, in DE-A 44 05 059, EP-A 353 409, EP-A 92 097 and DE-A 44 31 949.

Thus, (meth)acrylic acid can be prepared, inter alia, by the catalytic gas-phase oxidation of an alkane, alkanol, alkene or alkenal of 3 or 4 carbon atoms or a mixture of two or more thereof. (Meth)acrylic acid can be particularly advantageously prepared, for example, by catalytic gas-phase oxidation of propene, acrolein, tert-butanol, isobutene, isobutane, isobutyraldehyde or (meth)acrolein. In a preferred embodiment, the (meth)acrolein is prepared by C1/C3 condensation, as described in EP-B 58 927.

However, other possible starting compounds are those which first form the actual $C_3$–$C_4$ starting compound as an intermediate during the gas-phase oxidation. An example is the methyl ether of tert-butanol.

These starting materials, as a rule diluted with inert gases, such as nitrogen, $CO_2$, saturated hydrocarbons and/or steam, are passed, as a mixture with oxygen, at elevated temperatures (usually from 200 to 400° C.) and, if required, superatmospheric pressure, over transition metal mixed oxide catalysts (eg. containing Mo, V, W and/or Fe) and are converted into (meth)acrylic acid by oxidation.

Owing to the large number of parallel and subsequent reactions taking place in the course of the catalytic gas-phase oxidation and as a result of the inert diluent gases to be concomitantly used, however, the catalytic gas-phase oxidation does not give pure (meth)acrylic acid but a reaction mixture which essentially contains (meth)acrylic acid, the inert diluent gases, the alkane, alkanol, alkene or alkenal of 3 or 4 carbon atoms or a mixture of two or more thereof and byproducts, eg. water and acetic acid, from which the (meth)acrylic acid must be isolated.

In the novel process, this is done initially by condensation of the reaction gas obtained in stage A (stage B). A first aqueous solution, which contains the main amount of (meth) acrylic acid and a residual amount of alkane, alkanol, alkene or alkenal of 3 or 4 carbon atoms or the mixture of two or more thereof from the reaction gas, and a first gas phase, which contains the main amount of alkane, alkanol, alkene or alkenal of 3 or 4 carbon atoms or a mixture of two or more thereof and a residual amount of (meth)acrylic acid from the reaction gas, are obtained.

Such condensations of mixtures obtained in the gas-phase oxidation for the preparation of (meth)acrylic acid are likewise known from the prior art and are described, for example, in German Laid-Open Applications DOS 3,721, 865 and DOS 4,225,321.

There are no particular restrictions with regard to the temperature which may be used in the condensation in the novel process, provided that the temperature is established so that a first aqueous solution which contains the main amount of (meth)acrylic acid and a residual amount of alkane, alkanol, alkene or alkenal of 3 or 4 carbon atoms or the mixture of two or more thereof is obtained. In general, at an absolute pressure of from 1 to 1.5 bar, the condensation is carried out at about 100° C. or less, preferably from about 0 to about 100° C., particularly preferably from about 30 to about 80° C. If another pressure range is chosen, the temperature ranges must be adapted.

In the present application, the term main amount means that the concentration ratio (meth)acrylic acid/alkane, alkanol, alkene or alkenal of 3 or 4 carbon atoms or mixtures of two or more thereof is greater than in the reaction gas obtained according to stage A, ie. the amount of (meth) acrylic acid present is greater than the amount of (meth) acrylic acid present in the reaction gas. The term residual amount means that the concentration ratio (meth)acrylic acid/alkane, alkanol, alkene or alkenal of 3 or 4 carbon atoms or a mixture or two or more thereof is less than in the reaction gas obtained according to stage A, ie. the amount of (meth)acrylic acid is lower than the amount thereof in the reaction gas.

In a further embodiment of the condensation carried out in the present invention, the reaction gas is brought into contact, at the abovementioned temperatures, in direct countercurrent, with a part of the first aqueous solution obtained beforehand in the condensation or with an aqueous solution fed in from outside and containing (meth)acrylic acid.

The condensation can be carried out in one or more stages.

Any desired conventional apparatuses, for example packed towers, sieve tray towers, bubble cap towers or spray towers, may be used for carrying out the condensation described above. More exact information regarding the apparatuses which may be used appears in Ullmann's Enzyklopädie der Technischen Chemie, 4th Edition, Volume 3, pages 357–395, Reaktionsapparate für Gas-Flüssig-Reaktion.

The novel process furthermore comprises the absorption of the (meth)acrylic acid contained in the first gas phase by bringing this gas phase into contact with fresh water, a second aqueous solution, which contains (meth)acrylic acid and a second gas phase, which contains alkane, alkanol, alkene or alkenal of 3 or 4 carbon atoms or a mixture of two or more thereof, being obtained.

In order that the amount of water to be worked up in the present process and finally consumed is kept as small as possible, the amount of fresh water is preferably adjusted so that the concentration of the (meth)acrylic acid in the second aqueous solution is from about 1 to about 80, particularly preferably from about 5 to about 25, % by weight, as long as the absolute pressure is from 1 to 1.5 bar.

The absorption according to stage C is generally carried out at from about 20 to about 100° C., preferably from about 50 to about 70° C., as long as the absolute pressure is from about 1 to $1.5 \times 10^5$ Pa, it being necessary to modify the temperature appropriately at other pressures. The last-mentioned temperature range is preferred when the (meth) acrylic acid and other carboxylic acids contained in the first gas phase are to be selectively separated off from the alkane, alkanol, alkene or alkenal of 3 or 4 carbon atoms or the mixture of two or more thereof likewise present there.

To carry out the absorption, the first gas phase and the fresh water can be fed cocurrent or countercurrent, the latter variant being preferred.

Particularly preferably, the first gas phase is introduced at the lower end of the absorption apparatus while the fresh water is introduced at the top of the absorption apparatus.

Particularly suitable absorption apparatuses are commercial absorption columns, ie. the absorption column may be, for example, a valve tray column, bubble cap column or other spray-type column or a packed column which, if required, have conventional baffles which provide a sufficient mass or heat transfer surface.

Packed columns are preferred, among which packed columns having stacked packings are particularly advantageous. Packed columns having stacked packing are known per se to a person skilled in the art and are described, for example, in Chem. Ing. Tech. 58 (1986) No. 1, 19–31. According to the invention, the use of sheet metal and plate packing has proven advantageous. Stacked packings are distinguished in particular by a small pressure loss and ensure short residence times, which is advantageous in view of the high tendency of (meth)acrylic acid to polymerize.

Furthermore, the novel process comprises, as stage D, the extraction of the is second aqueous solution which contains (meth)acrylic acid by bringing said solution into contact with a solution which contains at least one alkane, alkanol, alkene or alkenal of 3 or 4 carbon atoms or a mixture of two or more thereof and forms a miscibility gap with the second aqueous solution, an organic phase, which contains (meth) acrylic acid and the main part of alkane, alkanol, alkene or alkenal of 3 or 4 carbon atoms or the mixture of two or more thereof, and a third aqueous solution, which contains a smaller part of alkane, alkanol, alkene or alkenal of 3 or 4 carbon atoms or the mixture of two or more thereof, being obtained.

As is evident from the above, the extraction according to stage D can be carried out by means of a solution which contains an alkane, alkanol, alkene or alkenal of 3 or 4 carbon atoms or a mixture of two or more thereof and furthermore forms a miscibility gap with the second aqueous solution. Preferably, the extraction according to stage D is carried out with a solution of the same substance or substances which was or were used in stage A for the preparation of a reaction gas which contains (meth)acrylic acid. For use in stage D, the above solution must additionally have the property of forming a miscibility gap with the second aqueous solution.

The term main part used above means that more than 50% by weight of the total amount of the alkane, alkanol, alkene or alkenal of 3 or 4 carbon atoms fed to stage D or of the mixture of two or more thereof are in the organic phase. Accordingly, smaller part means that less than 50% by weight, based on the total amount of the alkane, alkanol, alkene or alkenal of 3 or 4 carbon atoms fed to stage D or of the mixture of two or more thereof, are in the third aqueous solution.

Suitable substances for this purpose are preferably (meth) acrolein, isobutene, propene, propane, butane, isobutyraldehyde, the methyl ether of tert-butanol (MTBE) or a mixture of two or more thereof.

The solution which contains at least one alkane, alkanol, alkene or alkenal of 3 or 4 carbon atoms or a mixture of two or more thereof which can be converted into (meth)acrylic acid either consists completely of alkane, alkanol, alkene or alkenal of 3 or 4 carbon atoms or the mixture of two or more thereof or contains this as a mixture with other substances, eg. water and/or acetic acid. The solution may also have impurities used as a preparation process of the components, ie. need not be purified before the extraction.

Additives which improve the extraction effect may also be introduced into the solution. Examples are antifoams, eg. tallow fatty alcohol and other polyalcohols, demulsifiers, such as alkali metal chlorides, and surfactants and substances which extend the miscibility gap, such as higher alkanes, in particular those of 4 to 14 carbon atoms.

There are in principle no restrictions with regard to the concentration of the alkane, alkanol, alkene or alkenal of 3 or 4 carbon atoms which is contained in this solution or of the mixture of two or more thereof which can be converted into (meth)acrylic acid, but the concentration of this component or these components in the solution is or are preferably from about 50 to 100, particularly preferably from about 70 to about 99.9, in particular from about 90 to about 97, % by weight.

The solution defined above must in any case have a miscibility gap with the aqueous solution which contains (meth)acrylic acid.

In the novel process, it is preferable to use, for the extraction of (meth)acrylic acid, a solution of alkane, alkanol, alkene or alkenal of 3 or 4 carbon atoms or a mixture of two or more thereof, which can be used as a starting material for the (meth)acrylic acid synthesis and preferably has a concentration of from about 50 to 100, particularly preferably from about 70 to about 99.9, in particular from about 90 to about 97, % by weight of an alkane, alkanol, alkene or alkenal of 3 or 4 carbon atoms or a mixture of two or more thereof. (Meth)acrolein is particularly preferably used.

The alkane, alkanol, alkene or alkenal of 3 or 4 carbon atoms contained in this solution or the mixture of two or more thereof, a certain part of which is present in the third aqueous solution after the extraction, is preferably recovered by a thermal separation method, for example by stripping with steam or an inert gas, eg. nitrogen, air, carbon dioxide, exit gas from the (meth)acrylic acid preparation or a mixture of two or more thereof or by distillative recovery. The alkane, alkanol, alkene or alkenal of 3 or 4 carbon atoms or the mixture of two or more thereof is virtually completely transferred to the gas phase and can then be used for the preparation of (meth)acrylic acid according to stage A, if necessary after passing through further stages.

The wastewater obtained on carrying out the thermal separation method, for example the stripping of the third aqueous solution, contains only traces of further components, eg. citraconic acid or acetic acid, and can be discarded without problems.

There are also no restrictions at all with regard to the concentration of the (meth)acrylic acid in the second aqueous solution which contains (meth)acrylic acid. Preferably, the content of (meth)acrylic acid in solution is from about 1 to about 80, particularly preferably from about 5 to about 40, in particular from about 10 to about 30, % by weight. In addition to (meth)acrylic acid and water, this solution contains a small amount, as a rule less than about 3% by weight, of the alkane, alkanol, alkene or alkenal of 3 or 4 carbon atoms or the mixture of two or more thereof and a small amount, as a rule less than 10% by weight, of acetic acid.

As stated above, the extraction gives an organic phase which contains (meth)acrylic acid. The extraction is preferably carried out so that the main part of the (meth)acrylic acid used is present in this phase. In addition to (meth) acrylic acid, the organic phase also contains small amounts of water, acetic acid and high boilers, as well as the main part of the alkane, alkanol, alkene or alkenal of 3 or 4 carbon atoms or of the mixture of two or more thereof. The concentration of (meth)acrylic acid in this organic phase is in general from about 1 to about 80, preferably from about 5 to about 40, in particular from about 10 to about 30, % by weight.

There are no particular restrictions at all with regard to the temperature at which stage D of the novel process can be carried out. The only precondition is that it is possible that two phases, an organic and an aqueous phase, form at the chosen temperature and the chosen pressure. In general, the extraction according to stage D is carried out at from about 0 to about 150° C., preferably from about 30 to about 80° C., in particular from about 50 to about 70° C., superatmospheric pressure being employed at above the boiling point of the alkane, alkanol, alkene or alkenal of 3 or 4 carbon atoms or of the mixture of two or more thereof as extracting agent. When (meth)acrolein is used as the extracting agent, superatmospheric pressure is employed at above about 68° C. When another alkane, alkanol, alkene or alkenal of 3 or 4 carbon atoms or a mixture of two or more thereof is used, temperature and/or pressure must be modified as a function thereof.

All apparatuses which are generally used for extraction, as described, for example, in Ullmann's Enzyclopädie der Technischen Chemie, 4th Edition, Vol. 2, page 546 et seq., in particular page 560 et seq. (1972), can be used for carrying out the extraction. Particular examples are mixer-settler apparatuses, extraction columns, spray tower extraction columns, pulsed and unpulsed tray-type, packed and extraction apparatuses which employ centrifugal forces.

The aqueous solution which contains (meth)acrylic acid and the solution which contains at least one alkane, alkanol, alkene or alkenal of 3 or 4 carbon atoms or a mixture of two or more thereof can be brought into contact with one another by either the cocurrent, crosscurrent or countercurrent method, countercurrent contact being preferred.

The extraction can be carried out in one or more stages, and it is also possible to use combinations of extraction apparatuses.

The extraction according to stage D can be carried out continuously or batchwise.

As stated above, the alkane, alkanol, alkene or alkenal of 3 or 4 carbon atoms used for the extraction and present in a small amount in the third aqueous solution, or the mixture of two or more thereof, is preferably recovered from this solution after passing through the extraction, wastewater which is essentially free of (meth)acrylic acid and a sixth gas phase which contains alkane, alkanol, alkene or alkenal of 3 or 4 carbon atoms or a mixture of two or more thereof being obtained. In principle, all thermal separation methods are suitable as a method for recovering the alkane, alkanol, alkene or alkenal of 3 or 4 carbon atoms or the mixture of two or more thereof, stripping with inert gas, eg. nitrogen, air, carbon dioxide or an exit gas formed in the preparation of (meth)acrylic acid, or a mixture of these inert gases, being particularly preferred. It is particularly preferable to use the air required for the oxidation.

The stripping process is generally carried out at from about 30 to about 100° C., preferably from about 50 to about 80° C. This is true for an absolute pressure of 1 bar and must be modified for other pressures.

The amount of gas, temperature and pressure are generally established so that complete recovery of the alkane, alkanol, alkene or alkenal of 3 or 4 carbon atoms or of a mixture of two or more thereof is achieved.

The type of stripping apparatus used is subject to no specific restriction, and it is possible to use any desired conventional stripping apparatuses which permit gas-liquid contact, for example packed columns, sieve tray columns, bubble cap columns or other tray-type columns or spray towers. Other suitable spray apparatuses are described under the key word absorption column in EP-A 706 986, in column 3, lines 11 to 38, and in the prior art cited therein, which is hereby incorporated by reference into the present application.

As stated above, the (meth)acrylic acid contained in the organic phase is likewise recovered, for example by feeding the organic phase obtained in stage D to the condensation stage B. In this stage, the main amount of alkane, alkanol, alkene or alkenal of 3 or 4 carbon atoms or of the mixture of two or more thereof is converted into the gaseous state and the main amount of (meth)acrylic acid remains in the first aqueous solution.

It is also possible for the organic phase which contains (meth)acrylic acid to be separated thermally, for example by distillation/rectification, preferably utilizing the energy of the reaction gases, a fraction which contains (meth)acrylic acid and a fraction which contains the alkane, alkanol, alkene or alkenal of 3 or 4 carbon atoms or the mixture of two or more thereof being obtained.

In a further embodiment of the present invention, the first aqueous phase from stage B, which contains the main amount of (meth)acrylic acid present in the reaction gas and a residual amount of alkane, alkanol, alkene or alkenal of 3 or 4 carbon atoms present in the reaction gas or of the mixture of two or more thereof, is freed from the alkane, alkanol, alkene or alkenal of 3 or 4 carbon atoms or the mixture of two or more thereof by a thermal separation method or is brought into contact with an inert gas, ie. stripped, the alkane, alkanol, alkene or alkenal of 3 or 4 carbon atoms contained therein or the mixture of two or more thereof being removed, together with a part of the water present, as a third gas phase, and aqueous (meth) acrylic acid solution containing up to 100, preferably from about 50 to about 90, % by weight of (meth)acrylic acid being obtained.

To carry out this part-stage of the novel process as a stripping procedure, the first aqueous phase is passed into the middle part or the upper end of a stripping apparatus, preferably the upper end thereof. An inert gas, eg. nitrogen, air, carbon dioxide, exit gas formed in the gas-phase oxidation in preparation stage A, exit gas formed in the combustion of the first-mentioned exit gas, or a mixture of these inert gases, passed into the tower, preferably the lower part thereof, the amount of gas, temperature and pressure preferably being established so that a major part of the alkane, alkanol, alkene or alkenal of 3 or 4 carbon atoms present or of the mixture of two or more thereof is separated off.

The operating temperature of the stripping apparatus used is in general from about 150° C. or less, preferably from about 30 to about 150° C., in particular from about 80 to about 130° C., in each case at from about 1 to about $1.5 \times 10^5$ Pa, it being necessary here too for an appropriate modification to be made if other temperatures are chosen.

The type of stripping apparatus is not subject to any specific restrictions, and it is possible to use any desired conventional stripping apparatuses, preferably stripping towers, which permit very good gas-liquid contact, for example packed towers, sieve tray towers, bubble cap towers or spray towers. Regarding further details, reference may be made to Ullmann's Enzyklopädie der Technischen Chemie, Vol. 2, page 575 et seq., in particular page 587/8 and 589 et seq. (1972).

In this part-stage, the alkane, alkanol, alkene or alkenal of 3 or 4 carbon atoms contained in the first aqueous solution, or the mixture of two or more thereof, is virtually completely separated off and is obtained at the upper end of the stripping column in the form of a gas mixture (third gas phase), while an aqueous (meth)acrylic acid solution as defined above is obtained at the lower end of the apparatus.

The aqueous (meth)acrylic acid solution thus obtained may also contain small amounts (less than 20% by weight) of acetic acid and (less than 10% by weight) of high boilers.

The acetic acid and the high boilers can be removed in the further working s up of the resulting aqueous (meth)acrylic acid solution by processes known per se, as described, for example, in German Laid-Open Applications DOS 4,335,172 and DOS 4,201,697.

In particular, the working up of the resulting aqueous (meth)acrylic acid solution is carried out by crystallization. Crystallization of this type is described, inter alia, in DE-A 197 40 252.6, which is hereby fully incorporated by reference in the context of the present Application.

Nevertheless, the principles of the crystallization which may be carried out according to the invention is to be described below with reference to FIG. 3. According to the invention, a part of the total amount of the condensed MAS solution (B1) or of the solution (MA1) obtained in the methacrolein isolation (MA), in which the heavy boilers (SS) may also be separated off, can be subjected to a purification by crystallization.

The crystallization and solid-liquid separation (KR+FFT) gives (meth)acrylic acid crystals (KR1) which, depending on the purity, can be used as pure (meth)acrylic acid or for the preparation of (meth)acrylic esters.

The mother liquor arriving from stage KR+FFT contains byproducts, eg. acetic acid, in addition to water and (meth) acrylic acid. Some or all of this mother liquor can be removed from the process (ML1); for recovery of (meth) acrylic acid, some or all of the mother liquor can be fed to the (meth)acrylic acid extraction according to stage D (ML2) and/or to stage B (ML3) and/or to the methacrolein isolation (ML4).

Specifically, the following procedure is adopted:

In stage (KR+FFT), the solution obtained in stage (B) or (MA) and containing (meth)acrylic acid is crystallized. Here, no solvent is added, in particular no organic solvent. The crystallization method used is not subject to any restriction. The crystallization can be carried out continuously or batchwise, in one or more stages. The crystallization is preferably carried out in one stage. In another preferred embodiment, the crystallization is carried out as a fractional crystallization. In fractional crystallization, all stages which produce crystals which are purer than the aqueous (meth) acrylic acid solution fed in are usually referred to as purification stages and all other stages are referred to as expulsion stages. Here, multistage processes are advantageously operated according to the countercurrent principle in which, after the crystallization in each stage, the crystals are separated from the mother liquor and these crystals are fed to the respective stage with the next highest purity while the crystallization residue is fed to the respective stage with the next lowest purity.

Advantageously, the temperature of the solution during the crystallization is from −25 to +15° C., in particular from −15 to 5° C. The solids content in the crystallizer is advantageously from 0 to 90, preferably from 15 to 65, g of solid/100 g.

In a further advantageous embodiment, the crystallization is carried out by cooling apparatus walls or by partially evaporating the solution under reduced pressure. In the crystallization by cooling, the heat is removed via scratch coolers which may be connected to a stirred kettle or a container without a stirrer. Here, the crystal slurry is circulated by means of a pump.

It is also possible to remove the heat via the wall of a stirred kettle, in particular by means of a stirrer passing close to the wall. A further preferred embodiment of the crystallization by cooling is the use of cooling plate crystallizers as produced, for example, by GMF Gouda (The Netherlands). In a further suitable variant of the crystallization by cooling, the heat is removed via conventional heat exchangers (preferably tube-bundle or plate-type heat exchangers). In contrast to scratch coolers, stirred kettles having stirrers passing close to the wall or cooling plates, these apparatuses have no means for avoiding crystal layers on the heat-transmitting surfaces. During operation, a condition in which the heat transfer resistance assumes too high a value owing to the formation of crystal layers results in switching over to a second apparatus. During the operating time of the second apparatus, the first apparatus is regenerated (preferably by melting off the crystal layer or flushing the apparatus with unsaturated solution). An excessively high heat transfer resistance in the second apparatus results in switching back to the first apparatus, etc. This variant can also be operated cyclically with more than two apparatuses. Moreover, the crystallization may be effected by conventional partial evaporation of the solution under reduced pressure. In a further advantageous embodiment of the invention, the crystallization is carried out in apparatuses in which the crystals grow on cooled surfaces in the crystallization apparatus, ie. are fixed in the apparatus (for example, layer crystallization process of Sulzer Chemtech (Switzerland) or static crystallization process of BEFS PROKEM (France)).

The (meth)acrylic acid crystals obtained in stage (KR+FFT) are separated from the mother liquor. In the case of layer crystallization or static crystallization, the separation of the crystals from the mother liquor can take place in the crystallization apparatus itself since the crystals are fixed in the apparatus and the mother liquor can be removed by allowing it to flow out of the apparatus. The crystals are removed from the crystallization apparatus by melting the crystals and then allowing the melt to flow away. In the case of suspension crystallization, all known solid-liquid separation methods are suitable. In a preferred embodiment of the invention, the crystals are separated from the mother liquor by filtration and/or centrifuging. Advantageously, the slurry is prethickened, for example by hydrocyclone(s), before the filtration or centrifuging. All known centrifuges which operate batchwise or continuously are suitable for the centrifuging. The most advantageously used ones are pusher centrifuges which can be operated in one or more stages. Scroll conveyor centrifuges or helical conveyor centrifuges (decanters) are also used here. Filtration is advantageously carried out by means of suction filters which are operated batchwise or continuously, without or without a stirrer, or by means of belt filters. In general, filtration can be carried out under superatmospheric or reduced pressure.

During and/or after the solid-liquid separation, further process steps for increasing the purity of the crystals or of the crystal cake can be provided. In a particularly advantageous embodiment of the invention, the separation of the crystals from the mother liquor is followed by a one-stage or multistage washing and/or sweating of the crystals or of the crystal cake. During washing, the amount of wash liquid is suitably from 0 to 500, preferably from 30 to 200, g of wash liquid/100 g of crystals. The wash liquid used is subject to no restriction. Advantageously, however, washing is carried out using pure product, ie. using a liquid which contains (meth)acrylic acid whose purity is generally higher than that of the crystal cake to be washed, but has in any case a higher purity than the mother liquor in the crystallization. Washing with water is also possible. The washing can be carried out in apparatuses usually used for this purpose. Wash columns in which removal of the mother liquor and washing are carried out in one apparatus, centrifuges which can be operated in one or more stages or suction filters or belt filters are advantageously used. The washing can be carried out on centrifuges or belt filters in one or more stages. Here, the wash liquid can be fed countercurrent to the crystal cakes.

Sweating is local melting of contaminated regions. The extent of sweating is advantageously from 0 to 100, preferably from 5 to 35, g of molten crystals/100 g of crystals before the sweating. The sweating is particularly preferably carried out on centrifuges or belt filters. It may also be possible to carry out a combination of washing and sweating in one apparatus.

The third gas phase which is obtained during the stripping and contains alkane, alkanol, alkene or alkenal of 3 or 4 carbon atoms or a mixture of two or more thereof and water can, in the novel process, be introduced into condensation stage B and/or absorption stage C and further worked up there.

In a further embodiment of the present invention, the first gas phase, alone or together with the third gas phase, is divided, before the absorption according to stage C, into a circulation gas stream which is introduced into absorption stage C and an exit gas stream.

The exit gas stream can be subjected to condensation in a further additional stage E, a fourth aqueous solution, which contains the main amount of (meth)acrylic acid and a residual amount of alkane, alkanol, alkene or alkenal of 3 or 4 carbon atoms or the mixture of two or more thereof from the exit gas stream, and a fourth gas phase, which contains the main amount of alkane, alkanol, alkene or alkenal of 3 or 4 carbon atoms or the mixture of two or more thereof and a residual amount of (meth)acrylic acid from the exit gas stream, being obtained.

The process conditions of stage E and the apparatuses used there correspond to the conditions and apparatuses mentioned and discussed with respect to stage B.

Regarding the temperatures used for this condensation, the statements made with regard to stage B are also applicable, except that, in the condensation according to stage E, slightly lower temperatures are used, so that the temperature range preferred for this stage is from about 30 to about 50° C., in each case at from about 1 to about $1.5 \times 10^5$ Pa, it being necessary here too to make appropriate modifications if other temperatures are chosen.

In a further embodiment of the present invention, the fourth gas phase obtained in stage E can be subjected to an absorption stage F in which the alkane, alkanol, alkene or alkenal of 3 or 4 carbon atoms contained in the fourth gas phase or the mixture of two or more thereof is removed virtually completely from the fourth gas phase by bringing it into contact with a fifth aqueous solution which contains (meth)acrylic acid, an exit gas which is essentially free of (meth)acrylic acid, alkane, alkanol, alkene or alkenal of 3 or 4 carbon atoms or the mixture of two or more thereof and a circulation solution which is laden with alkane, alkanol, alkene or alkenal of 3 or 4 carbon atoms or a mixture of two or more thereof and contains (meth)acrylic acid being obtained.

The absorption stage F is essentially carried out similarly to absorption stage C, but it should be noted that temperatures used in absorption stage F are in general lower than the temperatures stated for absorption stage C, and the absorption according to stage F is generally carried out at from about 0 to about 50° C., preferably from about 4 to about 30° C., in each case at from about 1 to about $1.5 \times 10^5$ Pa, it being necessary here too for the appropriate modifications to be made if other temperatures are chosen.

The exit gas obtained in stage F can, if required, be used for stripping the alkane, alkanol, alkene or alkenal of 3 or 4 carbon atoms or the mixture of two or more thereof at various points in the novel process or can be fed—completely or partially—back into preparation stage A.

The alkane, alkanol, alkene or alkenal of 3 or 4 carbon atoms which is contained in the laden circulation solution or the mixture of two or more thereof can be desorbed by being brought into contact with a gas which contains an alkane, alkanol, alkene or alkenal of 3 or 4 carbon atoms or a mixture of two or more thereof, preferably with the circulation gas stream, a sixth aqueous solution, which contains (meth)acrylic acid, and a fifth gas phase, which contains the alkane, alkanol, alkene or alkenal of 3 or 4 carbon atoms or the mixture of two or more thereof, being obtained (stage G).

The laden circulation solution is passed into the lower part of the absorption apparatus for carrying out stage C. The desorption of the alkane, alkanol, alkene or alkenal of 3 or 4 carbon atoms or of the mixture of two or more thereof can of course also be carried out separately therefrom, although this is not preferable since this requires additional apparatus.

Regarding the desorption procedure according to stage G, reference may be made to the absorption according to stage C for the apparatuses and temperatures which may be used. In addition to the second aqueous solution obtained in the absorption according to stage C [(meth)acrylic acid absorption], the fourth aqueous solution obtained in the condensation according to stage E [(meth)acrylic acid condensation] or the laden circulation solution obtained in the absorption according to stage F [absorption of the alkane, alkanol, alkene or alkenal of 3 or 4 carbon atoms or of the mixture of two or more thereof] or the sixth aqueous solution obtained in the desorption according to stage G [desorption of the alkane, alkanol, alkene or alkenal of 3 or 4 carbon atoms or of the mixture of two or more thereof], each of which solutions contains (meth)acrylic acid and which individually or as a combination of two or more thereof, with or without the second aqueous solution, form at least one feed, can also be introduced into extraction stage D. It is preferable if the aqueous solutions described above are introduced together with the second aqueous solution into stage D.

In a further, preferred embodiment, the abovementioned aqueous solutions, each of which contains (meth)acrylic acid, are divided before the extraction according to stage D into a stream for water removal, which is introduced into the extraction stage D, and a circulation solution for scrubbing the exit gas. The ratio of the stream for water removal/circulation solution is preferably chosen so that the amount of fresh water fed to stage C is contained in the stream for water removal. The stream for water removal is then subjected to the extraction according to stage D, as described above, and further worked up.

While, as also mentioned above, the organic phase which contains (meth)acrylic acid is preferably fed to condensation stage B, the third aqueous solution which contains the alkane, alkanol, alkene or alkenal of 3 or 4 carbon atoms or the mixture of two or more thereof is brought into contact with an inert gas (stripping), a wastewater, which is essentially free of alkane, alkanol, alkene or alkenal of 3 or 4 carbon atoms or the mixture of two or more thereof, starting material and (meth)acrylic acid and may contain only traces of these two components and possibly acetic acid, and a sixth gas phase, which contains alkane, alkanol, alkene or alkenal of 3 or 4 carbon atoms or the mixture of two or more thereof, being obtained. The stripping gas is particularly preferably the air used for oxidation. However, another thermal separation operation may also be used.

Regarding the process conditions and apparatuses required for the stripping to obtain the sixth gas phase, reference may be made to the statements made above with respect to the removal of alkane, alkanol, alkene or alkenal of 3 or 4 carbon atoms or of the mixture of two or more thereof from the first aqueous solution and the detailed description of stage D, in which the working up of the third aqueous solution is also discussed.

Any circulation solution separated off and used for scrubbing the exit gas can also be treated by being brought into contact with an inert gas (stripping); it is particularly preferable to employ a part of the air used for oxidation, a regenerated circulation solution and a seventh gas phase which contains alkane, alkanol, alkene or alkenal of 3 or 4 carbon atoms or the mixture of two or more thereof being obtained.

The circulation solution or the regenerated circulation solution is preferably introduced into absorption stage F as the fifth aqueous solution which contains (meth)acrylic acid.

The gas phases obtained at various points in the present process, ie. the first, second, third, fifth, sixth and seventh gas phase, each of which contains alkane, alkanol, alkene or alkenal of 3 or 4 carbon atoms or the mixture of two or more thereof, can be introduced either individually or as a combination of two or more thereof into preparation stage A, complete recycling of these gas phases being preferred.

A conventional stabilizer, eg. phenothiazine or hydroquinone, or a derivative thereof, can of course be added to the organic phases or aqueous solutions to avoid or to reduce the polymerization tendency of the (meth)acrylic acid or of the alkane, alkanol, alkene or alkenal of 3 or 4 carbon atoms or of the mixture of two or more thereof.

A particularly preferred embodiment of the novel process for the preparation of (meth)acrylic acid with the use of methacrolein as an extracting agent for methacrylic acid is once again described below with reference to FIG. 1, the solid lines indicating liquid flows and the hatched lines gaseous flows:

In a reaction under heterogeneous catalysis, methacrolein (MAC) is oxidized with atmospheric oxygen to give methacrylic acid (MAS). Acetic acid (ES) is formed as a byproduct (stage A).

The reaction gas containing MAS, ES, MAC, $O_2$ (oxygen) and $H_2O$ (A1) is cooled in the reaction gas cooling (condensation according to stage B) and the main amount of the methacrylic acid contained in the reaction gas and the acetic acid are partially condensed. The resulting MAS solution (B1) is fed to the methacrolein isolation (MA). In the methacrolein isolation, MAC and water are separated from the MAS solution (B1) and the methacrylic acid is concentrated. The gas containing MAC and water is recycled to stage B (not shown).

The gas (B) (first gas phase) with the MAS and ES not removed in stage B contains the main amount of MAC and is divided into a circulation gas stream (B2) and an exit gas stream (B3).

The circulation gas stream first strips methacrolein in the methacrolein desorption (stage G) from the circulation solution (F1) used for scrubbing the exit gas and then passes to the methacrylic acid absorption (stage C).

In the methacrylic acid absorption, MAS and ES are separated from the circulation gas (B2/G2) and the oxidation air (MS1/R1) laden with MAC and MAS and ES, as discussed below, with fresh water, while MAC remains in the circulation gas. The circulation gas (C1) enriched with MAC and oxygen is recycled to stage A. Furthermore, an aqueous solution (C2) which contains MAS is obtained.

The exit gas stream (B3) is fed to the methacrylic acid condensation (stage E), a major part of the MAS and ES present therein condensing out (E1).

The gas phase (E2) obtained in this condensation is fed to the methacrolein absorption according to stage F, which will be described in more detail below.

The aqueous solutions C2, G1 (described below) and E1 from the methacrylic acid absorption, the methacrolein desorption and the methacrylic acid condensation are divided into a circulation solution for scrubbing the gas (K1) and a stream for removing the water (W).

Since the amount of water removed is determined by means of the water balance and the stream must also contain the MAS not in the condensation stage B, the concentration of MAS in the circulation solution varies. The MAS concentration in the circulation solution or in the stream for removing water can be adjusted depending on the amount of water fed in or removed.

The methacrylic acid and the predominant part of the acetic acid are separated from the stream for removing the water (W) in the methacrylic acid extraction (stage D) with the methacrolein solution (M) used as a starting material for the MAS preparation, an organic phase (D1), which contains the MAS and the main amount of the acetic acid, each of which is present in the stream for removing the water, and the main part of MAC, and an aqueous phase (D2), which contains a smaller part of MAC, being obtained.

The MAC dissolved in the aqueous phase (D2) is recovered in the methacrolein stripping (MS) by desorption with a part of the air required for the oxidation.

The organic phase (D1) which contains MAS, ES and MAC is introduced into the reaction gas cooling (B) and separated there. While MAC evaporates and thus reduces the cooling power, MAS remains in the liquid phase and increases the concentration of the MAS solution (B1) separated off in the reaction gas cooling.

In the regeneration (R), MAC is virtually completely separated from the circulation solution for scrubbing the exit gas (K1). The separation is achieved by stripping with a part of the air required for the oxidation.

The oxidation air from the methacrolein stripping of the discharge stream (MS1) and from the regeneration of the circulation solution (R1) is fed, together with the circulation gas (G2) passing through the methacrolein desorption according to stage G, into the methacrylic acid absorption (stage C).

The regenerated circulation solution (K2) is cooled and is used for the MAC absorption (stage F) from the exit gas stream (B3/E2). By means of the MAS content of the regenerated circulation solution (K2), the MAC solubility is improved in comparison to pure water and hence the methacrolein absorption is facilitated. After the methacrolein desorption according to stage G with the circulation gas (B2), the aqueous solution (G1) then obtained is recycled to the regeneration/extraction.

Figure 1:
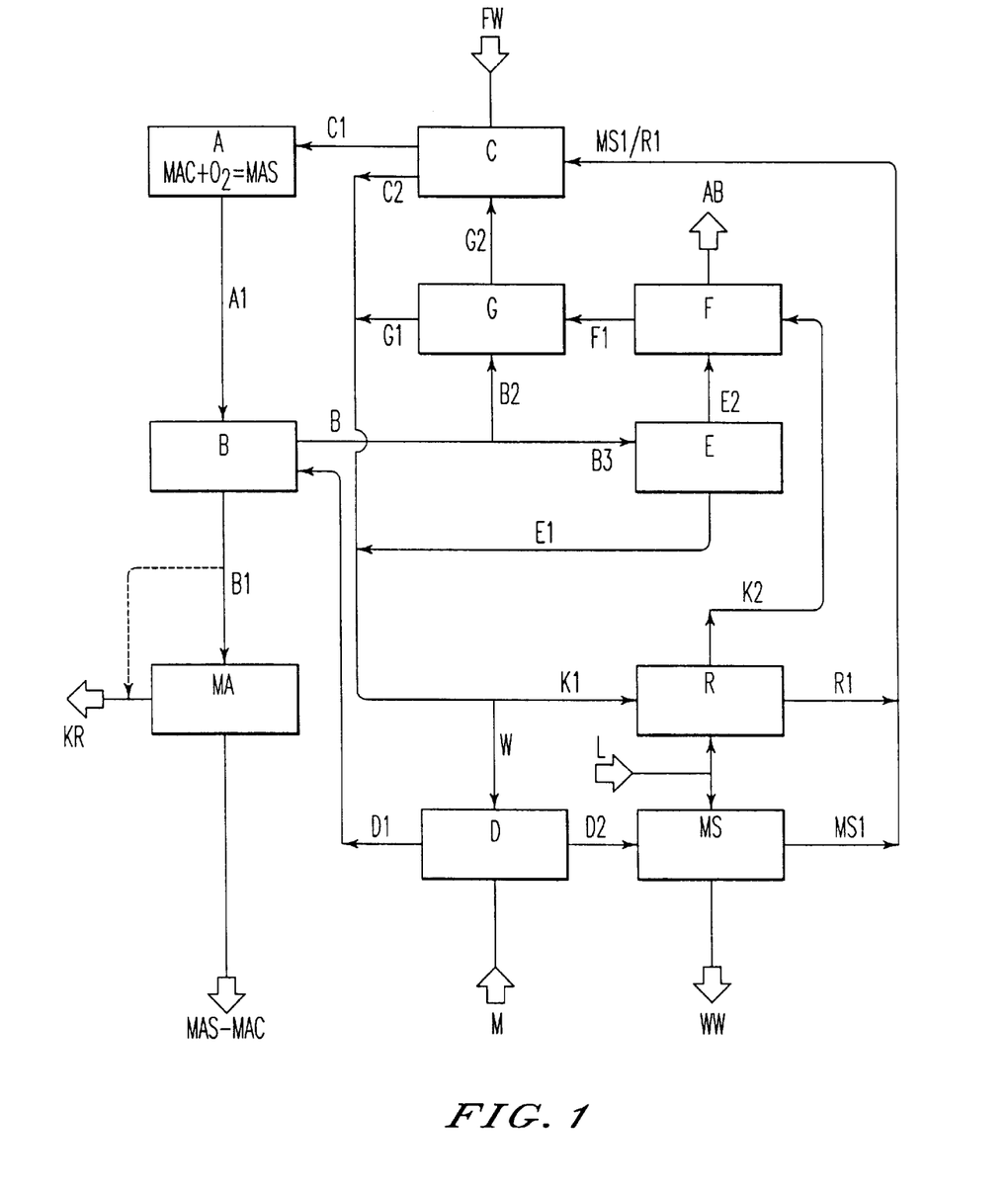
FIG. 1 shows a schematic diagram of a preferred embodiment of the novel process and is explained in more detail in the description.

In FIG. 1, the meanings are furthermore as follows:

AG—Exit gas

FW—Fresh water

Figure 3:
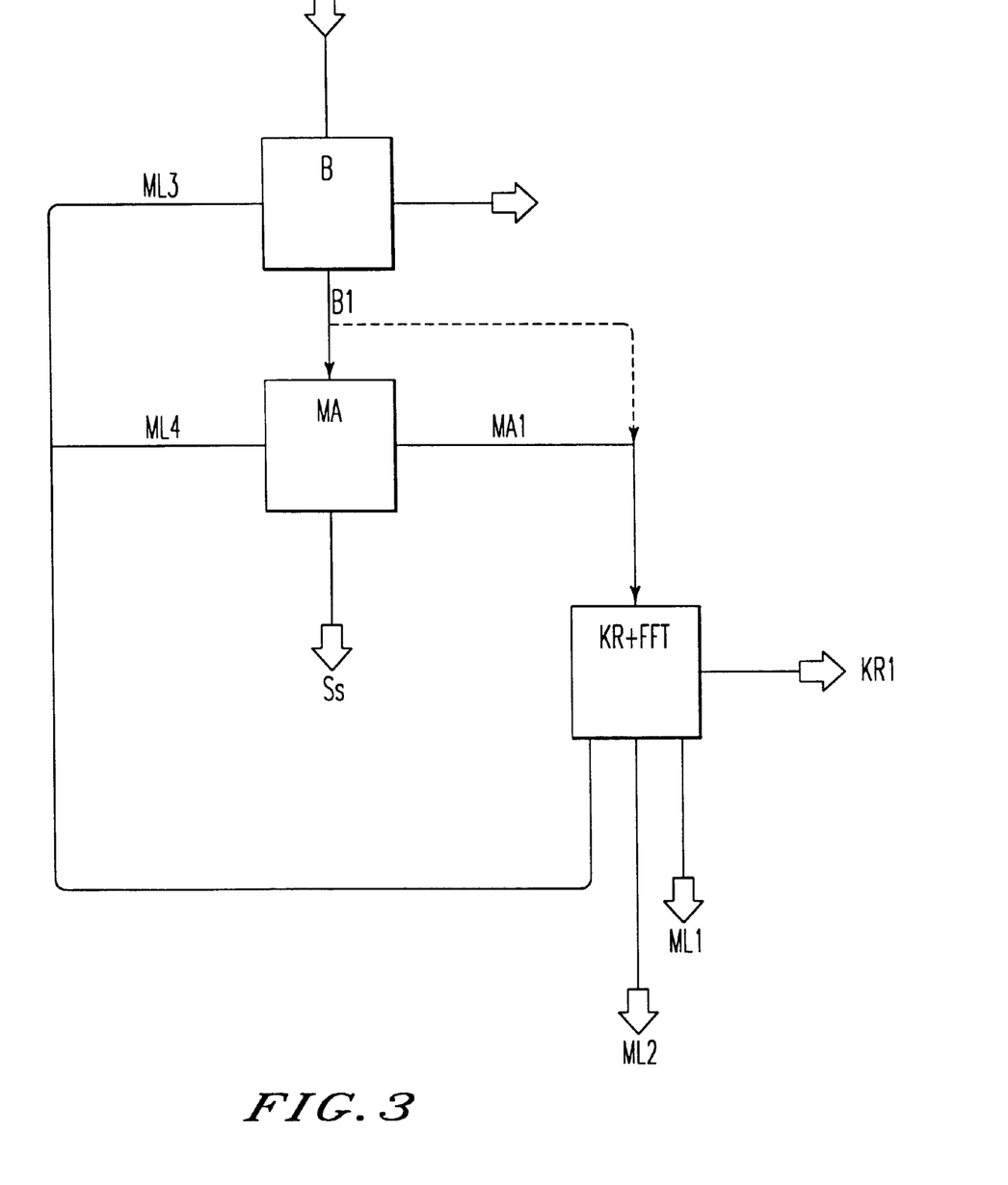
FIG. 3 supplements FIG. 1 and illustrates the is possible integration of a crystallization stage for obtaining pure (meth)acrylic acid into the novel process.

KR—Crystallization (cf. FIG. 3)

L—Air

MAS-MAC—Methacrylic acid solution without methacrolein

WW—Wastewater

EXAMPLE

Figure 2:
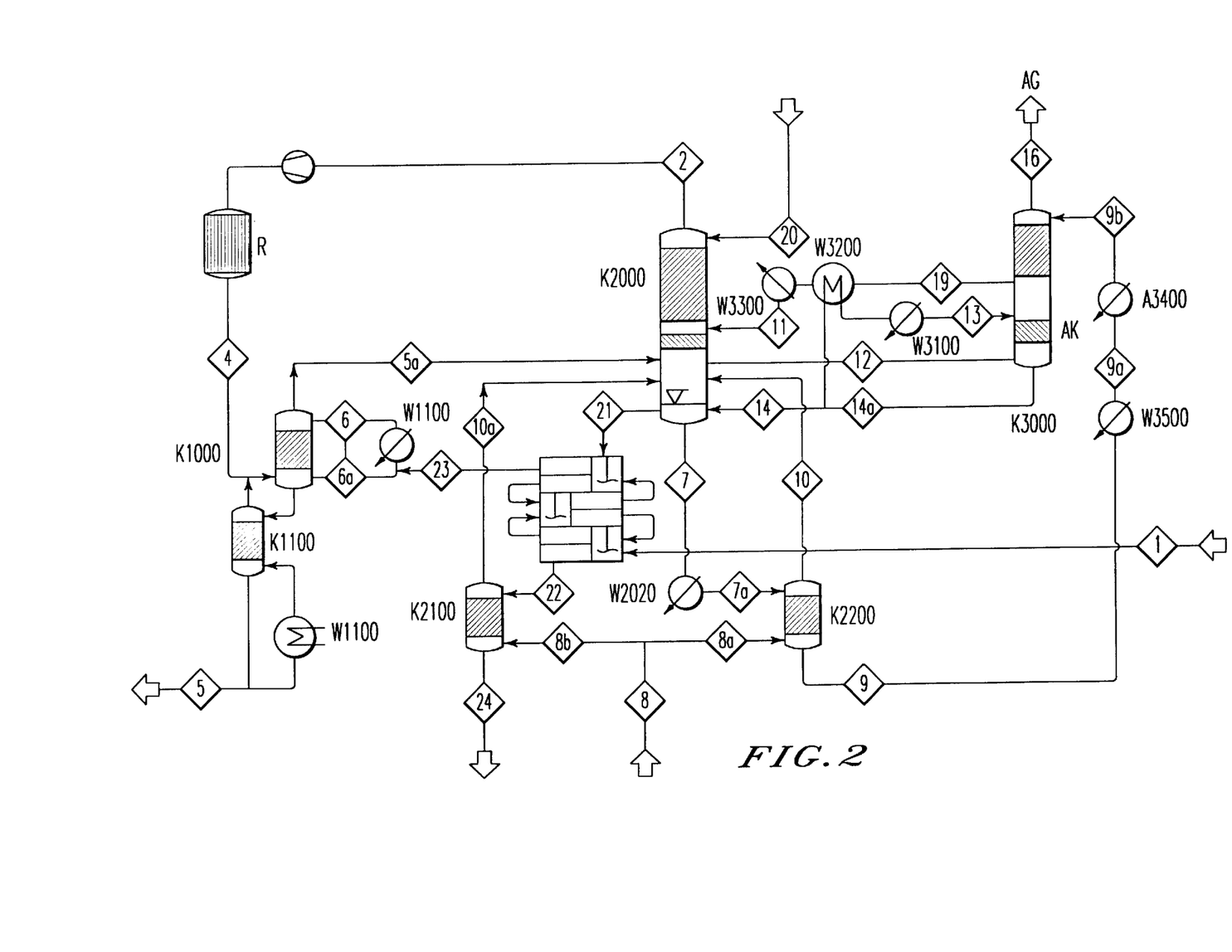
FIG. 2 shows a process flow diagram with the most important apparatuses and is explained in more detail in the discussion of the Example according to the invention.

An embodiment of the novel process is described below with reference to FIG. 2, the composition and the amount, density and temperature of the liquid and gaseous streams described below being shown in the attached table.

In an oxidation under heterogeneous catalysis, methacrolein (MAC) was oxidized to methacrylic acid (MAS) under formation of acetic acid (ES) as a byproduct in the reactor (R). The reaction gas (4) at about 220° C. was cooled to about 63° C. in quench column K 1000 (diameter 100 mm, 1000 mm Pall ring packing). About 70% by weight of methacrylic acid and 44% by weight of acetic acid, based in each case on the total amount of these two components present in the reaction gas, were condensed from about 30 kg/h of reaction gas. The reaction gas was cooled on the one hand by means of the cooler W 1100 in the liquid circulation (6a, 6) and, on the other hand, by evaporating methacrolein and water in quench column K 1000.

To prevent polymerization in quench column K 1000, hydroquinone was metered into the liquid circulation (6, 6a) as a stabilizer.

The MAC still present in the first aqueous solution from quench column K 1000 was removed in the MAC stripper K 1100 (diameter 30 mm, 500 mm Sulzer Mellapack), and an 80% strength by weight methacrylic acid solution was obtained (5).

That part of the reaction gas which was not condensed in quench column K 1000, together with the MAS and ES (5a) remaining there, was virtually completely separated off predominantly in the absorption column K 2000 (diameter 100 mm, 3000 mm Pall ring packing) with an amount (20) of fresh water reduced to 5 kg/h, while the starting material methacrolein remained in the circulation gas (2). By limited cooling of the quench column K 1000 and a thermostated addition of fresh water, a water content of 8.7% in the circulation gas was maintained at the top of the absorption column K 2000.

In the bottom of absorption column K 2000, the exit gas (12) was removed from the circulation gas stream and fed to the exit gas column K 3000.

Aqueous solution discharged from absorption column K 2000 was divided in a circulation stream (7/7a) of about 17.5 kg/h for scrubbing the exit gas and a stream of about 6.1 kg/h for removing water (21). Since the amount of the discharge stream was determined by the water balance and this stream must also contain the amount of MAS not condensed in quench column K 1000, the MAS concentration in the solution discharged from K 2000 increased. About 5 kg/h of fresh water resulted in an MAS concentration of about 15% by weight in the outflow from the absorption column K 2000, which greatly improved the MAC solubility in the circulation solution (7) for the MAC absorption.

The methacrylic acid was extracted from the discharge stream (21) with the methacrolein solution (2.9 kg/h) (1) used as a starting material for the MAS synthesis, with a three-stage mixer-settler cascade.

To recover the MAC discarded in the aqueous refined product (22), MAC was virtually completely stripped in the stripping column K 2100 (diameter 50 mm, 1000 mm Sulzer CY packing) with a part of the air (8/8b) used for the oxidation. A similar procedure was adopted with the circulation solution (7/7a) in the stripper K 2200.

The methacrolein solution (23) (organic phase) laden with about 23% by weight of MAS can be readily separated from the aqueous phase in the mixer-settler cascade and was fed to the liquid circulation (6a, 6) of quench column K 1000. In the latter, the methacrolein was evaporated from the extraction while the methacrylic and acetic acid remained in the liquid phase.

The circulation solution (7) used for scrubbing the exit gas was regenerated in stripping column 2200 (diameter 50 mm, 1000 mm Sulzer CY packing) by stripping with part of the air required for the oxidation.

Owing to the MAS content of about 15% by weight, the circulation solution (9, 9a, 9b) had to be cooled only to 15° C. in order to decrease the methacrolein concentration of the exit gas (16) to <1000 ppm in the exit gas column K 3000 (diameter 50 mm, 1000 mm Sulzer CY packing in the condensation section (AK) and 2000 mm Sulzer CY packing in the absorption section (MA)). The circulation solution (19) laden with more than 4% by weight of MAC was heated to about 62° C. in heat exchangers W 3200 and W 3300 and metered into the lower part of the circulation gas absorption column K 2000. Here, the major part of the (meth)acrolein absorbed from the exit gas was stripped into the circulation gas (2).

For better MAC absorption, the exit gas (12) was cooled to about 30° C. in the lower part of the exit gas column K 3000 (AK). The acids contained in the exit gas were for the most part condensed (14, 14a).

As is evident from the above, the novel process has in particular the following advantages:

the extraction of the (meth)acrylic acid can be carried out without the addition of foreign substances;

the process can be carried out without distillation stages, which are energy-intensive, and up to 100% strength by weight (meth)acrylic acid solution is obtained.

TABLE

Measured data from mini plant for the preparation of methacrylic acid by oxidation of methacrolein

| Stream | | 2 | 4 | 6 | 6a | 5a | 5 | 23 | 10 | 10a |
|---|---|---|---|---|---|---|---|---|---|---|
| Amount | kg/h | 30.0 | 30.0 | | 100.0 | | 3.5 | 3.9 | 5.4 | 1.9 |
| | MW | [w/w] | [w/w] | [w/w] | [w/w] | [w/w] | [w/w] | [w/w] | [w/w] | [w/w] |
| Water | 18.015 | 0.087 | | | 0.140 | | 0.137 | 0.070 | | |
| Methacrolein | 70.09 | 0.110 | 0.021 | | 0.004 | 0.107 | 0.002 | 0.683 | 0.023 | 0.037 |
| Methacrylic acid | 86.09 | | 0.093 | | 0.796 | 0.030 | 0.800 | 0.232 | | |
| Acetic acid | 60.05 | | 0.006 | | 0.036 | 0.003 | 0.036 | 0.010 | | |
| High boilers | | | | | 0.024 | | 0.024 | | | |
| Density | kg/m$^3$ | 1.4 | 1.2 | 990.4 | 973.2 | 1.5 | 953.8 | 841.8 | 1.4 | 1.4 |
| Temperature | °C. | 58.6 | 218.0 | 49.5 | 76.9 | 63.0 | 112.9 | 55.5 | 54.5 | 52.2 |
| Stream | | 20 | 11 | 12 | 14 | 21 | 7 | 1 | 22 | 24 |
| Amount | kg/H | 5.0 | | | 7.8 | 0.8 | 6.1 | 17.5 | 2.9 | 5.0 |
| | MW | [w/w] | [w/w] | [w/w] | [w/w] | [w/w] | [w/w] | [w/w] | [w/w] | [w/w] |
| Water | 18.015 | 1.00 | | | | | | | 0.071 | |
| Methacrolein | 70.09 | | 0.044 | 0.107 | 0.063 | 0.007 | 0.007 | | 0.920 | 0.0140 |
| Methacrylic acid | 86.09 | | 0.141 | 0.030 | 0.269 | 0.147 | 0.147 | | | 0.0006 |
| Acetic acid | 60.05 | | 0.015 | 0.003 | 0.029 | 0.016 | 0.016 | | 0.0110 | 0.011 |
| High boilers | | | | | | | | | | |
| Density | kg/m$^3$ | 985.5 | 954.2 | 1.1 | 974.5 | 978.4 | 978.4 | 824.1 | 982.9 | 989.9 |
| Temperature | °C. | 60.0 | 62.0 | 63.0 | 46.2 | 59.3 | 59.3 | 41.0 | 55.5 | 42.9 |
| Stream | | 7a | 9 | 8 | 9a | 13 | 14a | 9b | 19 | 16 |
| Amount | kg/h | 17.5 | 17.0 | 6.6 | 17.0 | 30.0 | 30.8 | 17.0 | | 6.0 |
| | MW | [w/w] | [w/w] | [w/w] | [w/w] | [w/w] | [w/w] | [w/w] | [w/w] | [w/w] |
| Water | 18.015 | | 0.836 | 0.010 | | | | | 0.798 | 0.008 |
| Methacrolein | 70.09 | 0.007 | 0.00003 | | 0.000 | 0.063 | 0.063 | 0.000 | 0.044 | 0.000 |
| Methacrylic acid | 86.09 | 0.147 | 0.148 | | 0.148 | 0.269 | 0.269 | 0.148 | 0.141 | 0.001 |
| Acetic acid | 60.05 | 0.016 | 0.016 | | 0.016 | 0.029 | 0.029 | 0.016 | 0.015 | |
| High boilers | | | 0.000 | | | | | | | |
| Density | kg/m$^3$ | 979.9 | 991.7 | 1 | 996.3 | 983.5 | 974.5 | 1001.3 | 987.9 | 1.6 |
| Temperature | °C. | 57.0 | 44.6 | 70.0 | 30.0 | 30.0 | 46.2 | 15.0 | 26.2 | 15.1 |

We claim:

1. A process for preparing (meth)acrylic acid comprising:
  a) preparing a gas comprising (meth)acrylic acid, water, oxygen and at least one of an alkane, an alkanol, an alkene or an alkenal of 3 or 4 carbon atoms;
  b) condensing said gas to obtain:
    i) a first aqueous solution comprising (meth)acrylic acid; and
    ii) a first gas phase;
  c) contacting said first gas phase with fresh water to form a second aqueous solution and a second gas phase; and
  d) extracting said second aqueous solution with an extraction solution which comprises at least one of an alkane, an alkanol, an alkene or an alkenal of 3 to 4 carbon atoms and which forms a miscibility gap with said second aqueous solution to form an organic phase comprising (meth)acrylic acid and a third aqueous phase.

2. The process of claim 1, wherein said gas is prepared by gas-phase oxidation of at least one of an alkane, an alkanol, an alkene, or an alkenal of 3 or 4 carbon atoms, under heterogenous catalysis.

3. The process of claim 1, wherein said first aqueous solution comprises (meth)acrylic acid and a residual amount of at least one of an alkane, an alkanol, an alkene or an alkenal of 3 or 4 carbon atoms.

4. The process of claim 1, wherein said first gas phase comprises at least one of an alkane, an alkanol, an alkene or an alkenal of 3 or 4 carbon atoms and a residual amount of (meth)acrylic acid.

5. The process of claim 1, wherein said second aqueous solution comprises (meth)acrylic acid.

6. The process of claim 1, wherein said second gas phase comprises at least one of an alkane, an alkanol, an alkene or an alkenal of 3 or 4 carbon atoms.

7. The process of claim 1, wherein said organic phase comprises (meth)acrylic acid and at least one of an alkane, an alkanol, an alkene or an alkenal of 3 or 4 carbon atoms.

8. The process of claim 3, further comprising separating said first aqueous solution into an aqueous solution of (meth)acrylic acid and a third gas phase comprising at least one of an alkane, an alkanol, an alkene or an alkenal of 3 or 4 carbon atoms.

9. The process of claim 8, further comprising introducing said third gas phase into stage b) with said reaction gas or stage c) with said first gas phase.

10. The process of claim 1, further comprising separating said first gas phase into a circulation gas stream which is introduced into stage c) and an exit gas stream.

11. The process of claim 9, further comprising separating said first and third gas phases into a circulation gas stream which is introduced into stage c) and an exit gas stream.

12. The process of claim 10 or 11, further comprising condensing said exit gas to obtain a fourth aqueous solution comprising (meth)acrylic acid and a fourth gas phase which comprises at least one of an alkane, an alkanol, an alkene or an alkenal of 3 or 4 carbon atoms and a residual amount of (meth)acrylic acid.

13. The process of claim 12, further comprising contacting said fourth gas phase with a fifth aqueous solution comprising (meth)acrylic acid to obtain:
  i) an exit gas which is essentially free of (meth)acrylic acid; and
  ii) a laden circulation solution comprising (meth)acrylic acid and at least one of an alkane, an alkanol, an alkene or an alkenal of 3 or 4 carbon atoms.

14. The process of claim 13, further comprising contacting said laden circulation solution with a gas comprising at least one of an alkane, an alkanol, an alkene or an alkenal of 3 or 4 carbon atoms to obtain:

i) a sixth aqueous solution comprising (meth)acrylic acid; and ii) a fifth gas phase comprising at least one of an alkane, an alkanol, an alkene or an alkenal of 3 or 4 carbon atoms.

15. The process of claim 14, wherein said extraction solution is selected from the group consisting of said forth aqueous solution, said laden circulation solution, said sixth aqueous solution and a mixture thereof.

16. The process of claim 10 or 11, wherein a portion of said second aqueous solution from stage c) is used as a circulation solution for scrubbing said exit gas.

17. The process of claim 1, further comprising introducing said organic phase into said condensation stage b).

18. The process of claim 1, wherein said extraction solution comprises 50–100% by weight of at least one of an alkane, an alkanol, an alkene or an alkenal of 3 or 4 carbon atoms.

19. The process of claim 1, wherein said third aqueous phase is contacted with an inert gas to produce a waste water and a sixth gas phase comprising at least one of an alkane, an alkanol, an alkene or an alkenal of 3 or 4 carbon atoms.

20. The process of claim 16, wherein said circulation solution is regenerated by contacting with an inert gas to obtain a regenerated circulation solution and a seventh gas phase comprising at least one of an alkane, an alkanol, an alkene or an alkenal of 3 or 4 carbon atoms.

21. The process of claim 13, wherein said fifth aqueous solution is a portion of said second aqueous solution from stage c).

22. The process of claim 13, wherein said fifth aqueous solution is a regenerated circulation solution obtained by contacting said laden circulation solution with an inert gas.

23. The process of claim 1, further comprising introducing at least one of said first and second gas phases into stage a).

24. The process of claim 8, further comprising introducing said third gas phase into stage a).

25. The process of claim 14, further comprising introducing said fifth gas phase into stage a).

26. The process of claim 19, further comprising introducing said sixth gas phase into stage a).

27. The process of claim 20, further comprising introducing said seventh gas phase into stage a).

* * * * *

UNITED STATES PATENT AND TRADEMARK OFFICE
CERTIFICATE OF CORRECTION

PATENT NO. : 6,051,736
DATED : April 18, 2000
INVENTOR(S) : Armin Schraut et al.

It is certified that error appears in the above-identified patent and that said Letters Patent is hereby corrected as shown below:

On the title page, item [75], the 3rd Inventor's name is misspelled. The Inventors should read as follows:

--[75] Inventors: Armin Schraut, Bensheim; Michael-Dieter Ulbrich, Freinsheim; Friedrich-Georg Martin, Heidelberg; Bernd Eck, Viernheim; Jörg Heilek, Bammental, all of Germany--

Signed and Sealed this

Tenth Day of April, 2001

*Attest:*

NICHOLAS P. GODICI

*Attesting Officer*     *Acting Director of the United States Patent and Trademark Office*